United States Patent [19]

Muel et al.

[11] Patent Number: 4,880,940

[45] Date of Patent: Nov. 14, 1989

[54] 4-ALKOXY-3-PYRROLIN-2-ON-1-YL ACETIC ACID ALKYL ESTERS

[75] Inventors: Thomas Muel; Leander Tenud, both of Visp; Laurent Duc, Sion; John McGarrity, Visp, all of Switzerland

[73] Assignee: Lonza Ltd., Gampel/Valais, Switzerland

[21] Appl. No.: 147,275

[22] Filed: Jul. 22, 1988

Related U.S. Application Data

[63] Continuation of Ser. No. 907,012, Sep. 15, 1986, abandoned.

[30] Foreign Application Priority Data

Sep. 24, 1985 [CH] Switzerland .......................... 4119/85
May 14, 1986 [CH] Switzerland .......................... 1958/86
Jun. 19, 1986 [CH] Switzerland .......................... 2486/86

[51] Int. Cl.$^4$ ............................................. C07D 207/38
[52] U.S. Cl. .................................................... 548/544
[58] Field of Search ......................................... 548/544

[56] References Cited

U.S. PATENT DOCUMENTS

| | | | |
|---|---|---|---|
| 2,535,010 | 12/1950 | Croxall et al. ...................... | 260/484 |
| 2,784,191 | 3/1957 | Fischer et al. ...................... | 260/294.7 |
| 4,118,396 | 10/1978 | Pifferi et al. ................... | 260/326.43 |
| 4,124,594 | 11/1978 | Monguzzi et al. .................. | 260/326 |
| 4,173,569 | 11/1979 | Banfi et al. .......................... | 260/326 |

FOREIGN PATENT DOCUMENTS 192255 2/1986 European Pat. Off. .
850007 11/1952 Fed. Rep. of Germany .
183756 11/1982 Japan .

OTHER PUBLICATIONS

Katsuki et al., "Bulletin of the Chemical Society of Japan", vol. 49, pp. 3287-3290 (1976).
Sidgwick, "The Organic Chemistry of Nitrogen", 3rd Ed., Oxford (1966), p. 637.
Ho et al., "Cleavage of Ester and Ether with Iodotrimethylsilane", Angewandte Chemie, vol. 15, No. 12 (1976), pp. 774 and 775.
Cram et al., J. Am. Chem. Soc., 1963, 85, pp. 1430-1437.
Lowe, J. Chem. Soc., Perkin Trans. I, 1973, 2907-2910.
Koehler Dissertation Bayreuth (1985).
MacKenzie et al., J.O.C.S. 20, No. 12 (1955), pp. 1695 and 1696.
CA:105:226341 (based upon European '255).
Lowe, J. Chem. Soc., Perkin Trans. I, 1973, 2907-2910.
G. Pifferi et al., II Farmaco, Ed. Sc. (1977), vol. 32, 602.

Primary Examiner—David B. Springer
Attorney, Agent, or Firm—Fisher, Christen & Sabol

[57] ABSTRACT

4-Alkoxy-3-pyrrolin-2-on-1-yl acetic acid alkyl esters are intermediate products for the production of cerebrally-active pharmaceutical products. The advantageous process for production of the new intermediate products is described.

3 Claims, No Drawings

4-ALKOXY-3-PYRROLIN-2-ON-1-YL ACETIC ACID ALKYL ESTERS

This is a continuation of Ser. No. 907,012, filed on 9/15/86, now abandoned.

The subject application is related to the commonly-owned application Ser. No. 907,011 entitled, "Process for the Production of 4-alkoxy-3-pyrrolin-2-ones" which was filed on Sept. 15, 1986, now abandoned. The pertinent parts of said commonly-owned application Ser. No. 907,011 are incorporated herein by reference.

BACKGROUND OF THE INVENTION

1. Field of the Invention

The invention relates to new 4-alkoxy-3-pyrrolin-2-on-1-yl acetic acid alkyl esters and to processes for producing them.

2. Prior art

A process for production of cerebrally-active 4-hydroxy-2-oxo-pyrrolidin-1-yl acetamide is known from Pifferi et al., II Farmaco, Ed. Sc., (1977), 32, 602. However, a poor yield and costly initial products make said process economically unfeasible.

BROAD DESCRIPTION OF THE INVENTION

The main object of the invention is to provide a production process which eliminates the disadvantages of the above-mentioned prior art process. Other advantages and objects of the processes and intermediate products of the invention are set out herein or are obvious herefrom to one skilled in the art.

The objects and advantages of the invention are achieved by the processes and intermediate products of the invention.

Unexpectedly, such objects and advantages can be attained by the discovery of the new intermediate products, namely, 4-alkoxy-3-pyrrolin-2-on-1-yl acetic acid alkyl esters having the general formula:

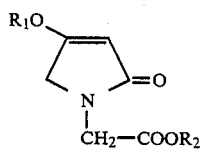

wherein $R_1$ is an alkyl having 1 or 2 C atoms and $R_2$ is an alkyl with 1 to 4 C atoms.

The preferred intermediate product is 4-methoxy-3-pyrrolin-2-on-1-yl acetic acid ethyl ester of the formula:

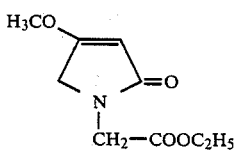

The 4-alkoxy-3-pyrrolin-2-on-1-yl acetic acid alkyl esters are valuable, stable intermediate products for the synthesis of cerebrally-active 4-hydroxy-2-oxo-pyrrolidin-1-yl acetamide.

The new 4-alkoxy-3-pyrrolin-2-on-1-yl acetic acid alkyl esters, preferably 4-methoxy-3-pyrrolin-2-on-1-yl acetic acid alkyl esters, are produced by the simple process comprising reacting 4-halo aceto acetic-$(C_1-C_4)$-alkyl ester, especially with an orthoformic acid-$(C_1-C_2)$-trialkyl ester, in an acid medium. The resultant 4-halo-3-$(C_1-C_2)$-alkoxy-2-E-butenoic acid-$(C_1-C_4)$-alkyl ester can be optionally isolated. Then, the latter ester is reacted either directly with a glycine-$(C_1-C_4)$-alkyl or benzyl ester in the presence of a base to the end product, or indirectly first, with aqueous ammonia solution to 4-$(C_1-C_2)$-alkoxy-3-pyrrolin-2-one and further, with 2-bromoacetic-$(C_1-C_4)$-alkyl or benzyl ester in the presence of an alkali hydride to the end product.

In the first step, a 4-halo aceto acetic-$(C_1-C_4)$-alkyl ester, preferably a 4-chloro aceto acetic acid-$(C_1-C_4)$-alkyl ester, especially preferably 4-chloro aceto acetic acid methyl ester, is reacted with orthoformic acid-$(C_1-C_2)$-trialkyl ester, preferably with orthoformic acid trimethyl ester, in an acid medium. Sulfuric acid, sulfonic acids or an acid ion exchanger are advantageously used as the acid.

The resultant 4-halo-3-$(C_1-C_2)$-alkoxy-2-E-butenoic acid-$(C_1-C_4)$-alkyl ester can be isolated. The further reaction can be performed either directly with a glycine-$(C_1-C_4)$-alkyl or benzyl ester in the presence of a base to end product, or indirectly first, with aqueous ammonia solution to 4-$(C_1-C_2)$-alkoxy-3-pyrrolin-2-one and further, with 2-bromoacetic-$(C_1-C_4)$-alkyl or benzyl ester in the presence of an alkali hydride to the end product.

If the direct way is chosen by reaction of the haloalkoxybutenoic acid ester with glycine ester, it is advantageous to use a weak inorganic base or tertiary aliphatic amine as the base. For example, sodium acetate, potassium carbonate or potassium hydrogencarbonate are particularly preferred representatives of the weak inorganic bases. Triethylamine can be used as a suitable representative of the tertiary aliphatic amines.

Further, it is advantageous to perform the reaction in a solvent. Aprotic or protic solvents with high polarity are advantageously used for this purpose. Suitable representatives are, e.g., acetonitrile, propionitrile, butyronitrile, diethylene glycol monomethyl ether, diethylene glycol dimethyl ether, N,N'-dimethylformamide or N,N'-dimethylacetamide.

The glycine-$(C_1-C_4)$-alkyl or benzyl ester is advantageously used in an amount of 1 to 4 mol, preferably from 1.25 to 2 mol per mol of the haloalkoxybutenoic acid ester used.

The hydrohalide, preferably the hydrochloride of the glycine alkyl ester, is advantageously used.

Then it is necessary, before reaction with the haloalkoxybutenoic acid ester, to convert the glycine alkyl ester hydrohalide into the free glycine alkyl ester by treatment with a base, e.g., a trialkylamine, preferably triethylamine, or an alkali methylate, such as sodium methylate.

The reaction temperature is advantageously chosen between 60° and 120° C. If the boiling temperature of the solvent so allows (as, e.g., in the case of acetonitrile), it is possible to work at the reflux temperature.

After completion of the reaction, the product is worked up in a conventional or usual way, e.g., by extraction and, optionally, by a subsequent recrystallization.

Using the process according to the invention, yields that generally exceed 80 percent are attained. The contents of the resultant products are usually above 95 percent.

If the indirect way is chosen, in a first step, the 4-halo-3-($C_1$–$C_2$)-alkoxy-2-E-butenoic acid-($C_1$–$C_4$)-alkyl ester is reacted advantageously with an aqueous NH$_3$ solution having a concentration of advantageously 10 to 25 percent, preferably 15 to 25 percent. The reaction temperature is advantageously between 20° and 100° C., preferably between 60° and 80° C. The molar ratio of 4-halo-3-($C_1$–$C_2$)-alkoxy-2-E-butenoic acid-($C_1$–$C_4$)-alkyl ester to NH$_3$ is advantageously between 1 to 2 and 1 to 5, advantageously between 1 to 2.5 and 1 to 3.5.

After a conventional or usual working up, e.g., by extraction with suitable solvents from the group of halogenated hydrocarbons, such as, methylene chloride and chloroform, the corresponding 4-($C_1$–$C_2$)-alkoxy-3-pyrrolin-2-one can be obtained in yields of about 90 percent in relation to the 4-halo aceto acetic acid-($C_1$–$C_4$)-alkyl ester.

It can optionally be used for the last stage, after additional purification by, e.g. recrystallization in aromatic hydrocarbons, preferably toluene. Therein the 4-($C_1$–$C_2$)-alkoxy-3-pyrrolin-2-one, preferably 4-methoxy-3-pyrrolin-2-one is reacted with a 2-bromacetic acid-($C_1$–$C_4$)-alkyl ester or a 2-bromoacetic acid benzyl ester, preferably with 2-bromoacetic acid ethyl ester, in the presence of an alkali hydride, advantageously with sodium hydride. The molar ratio of the compounds used, that is, 4-($C_1$–$C_2$)-alkoxy-3-pyrrolin-2-one to 2-bromoacetic acid-($C_1$–$C_4$)-alkyl ester, or 2-bromoacetic acid benzyl ester, to alkali hydride, is advantageously between 1 to 1 to 1 and 1 to 1.5 to 1.4, preferably between 1 to 1.2 to 1.2 and 1 to 1.4 to 1.4. The reaction temperature is advantageously between 0° and 50° C. The reaction is advantageously performed in a solvent which is inert toward alkali hydrides, a solvent such as acetonitrile, tetrahydrofuran, dimethoxyethane or dimethylformamide, preferably acetonitrile or dimethylformamide. It is also advantageous to work under a protective gas such as nitrogen or argon.

After a conventional or usual working up, e.g., by extraction, with optional subsequent purification by crystallization, the intermediate products according to the invention can also be obtained, in this way, with a very good yield.

DETAILED DESCRIPTION OF THE INVENTION

As used herein, all parts, percentages, ratios and proportions are on a weight basis unless otherwise stated herein, or otherwise obvious herefrom to one ordinarily skilled in the art.

EXAMPLE 1

(a) Production of 4-chloro-3-methoxy-2-E-butenoic acid methyl ester 31.0 g (0.2 mol) of 4-chloro aceto acetic acid methyl ester was mixed with 106.0 g (1.0 mol) of orthoformic acid trimethyl ester. 30.0 g of Amberlyst-15 ion exchange resin was added under argon with stirring. The reaction temperature rose to 40° C. with vigorous development of gas. After 5 hours of stirring, no educt could any longer be detected by thin-layer chromatography. The ion exchange resin was filtered off, and the residue was distilled in a water jet vacuum. The distillate was mixed with 1.0 g of p-toluenesulfonic acid monohydrate and slowly heated to 150° C., whereby methanol distilled off. The reaction mass was then distilled in a water jet vacuum. 24.7 g of a colorless liquid with a boiling point bp$_{12}$=93° C. was obtained.

NMR (CDCl$_3$)=5.16 (s, 1H); 4.67 (s, 2H); 3.73 (s, 6H). Yield: 75 percent.

(b) Production of 4-methoxy-3-pyrrolin-2-one 32.9 g (0.2 mol) of 4-chloro-3-methoxy-2-E-butenoic acid methyl ester was mixed with 82.0 g (1.2 mol) of 25 percent aqueous NH$_3$ solution and heated to 80° C. with vigorous stirring. After 1 hour of additional stirring, the mixture was allowed to cool to room temperature and the aqueous solution was extracted four times, each with 200.0 ml of methylene chloride. After drying the organic phase over Na$_2$SO$_4$, it was filtered, evaporated, and the residue was recrystallized hot from 120.0 ml of toluene. 16.9 g of white, crystalline product having a melting point of 132° to 133° C. was obtained.

NMR (CDCl$_3$)=6.92 (br. s, 1H); 5.07 (s. 1H); 3.93 (s. 2H); 3.82 (s, 3H). Yield: 74.8 percent.

(c) Production of 4-methoxy-3-pyrrolin-2-on-1-yl acetic acid ethyl ester 11.3 g (0.1 mol) of 4-methoxy-3-pyrrolin-2-one and 24.2 g (0.137 mol) of bromoacetic acid ethyl ester (95 percent) were suspended in 150.0 ml of acetonitrile. The suspension was mixed with 4.1 g (0.137 mol) of 80 percent sodium hydride at 0° C. Then the reaction solution was allowed to warm to room temperature, and was stirred for 90 minutes more. After evaporation of the solvent, the residue was suspended with 150.0 ml of ice water and extracted four times, each with 400.0 ml of methylene chloride. After a conventional or usual working up, the residue was mixed with 100.0 ml of petroleum ether (50° to 70° C.) and kept in a refrigerator overnight. The product crystallized out, was filtered by suction and was dried in a high vacuum. 19.6 g of yellowish colored product with a melting point of 55° to 58° C. was obtained.

NMR (CDCl$_3$)=5.11 (s, 1H); 4.69 (q, J=7.0 Hz, 2H); 4.66 (s, 2H); 3.99 (3, 2H); 3.83 (s, 3H); 1.28 (t, J=7.0 Hz, 3H); MS (70 eV)m/z =199 (M+, 25); 126(100). Yield: 98.5 percent.

EXAMPLE 2

(a) Production of 4-methoxy-3-pyrrolin-2-one

A solution of 63.3 g (0.409 mol) of 4-chloro aceto acetic acid methyl ester and 54.0 g (0.508 mol) of orthoformic acid methyl ester was cooled to 10° C. and mixed with 2.0 g (0.02 mol) of concentrated H$_2$SO$_4$ within 10 minutes. It was stirred for 5 hours at room temperature. Then the volatile products were distilled off at a vacuum of 25 mbar. Then the residue was heated at 125° C. and 100 mbar for 2.5 hours. During this time, 10.5 g of methanol distilled off. The residue was added drop by drop to a solution of 121.3 g of (17 percent) concentrated NH$_3$ solution in 83.7 g of water, within 1.75 hours, at 64° to 68° C. After half of the addition, 24.3 g of (17 percent) concentrated NH$_3$ solution was added. When the addition was completed, the reaction solution was stirred at 65° C. for 45 minutes more. Then the reaction solution was cooled to room temperature and continuously (12 hours) extracted with 300 ml of methylene chloride. The methylene chloride solution was dried over Na$_2$SO$_4$ and filtered off. After evaporation of the solution under vacuum, the crystalline residue was recrystallized hot from 150 ml of toluene. 40.8 g of white, crystalline product having a melting point of 130° to 132° C. [content (GC): 99.0 percent] was obtained. This corresponds to a yield of 87.4 percent.

(b) Production of 4-methoxy-3-pyrrolin-2-on-1-yl acetic acid ethyl ester 4.27 g of 4-methoxy-3-pyrrolin-2-one and 8.30 g of bromoacetic acid ethyl ester were dissolved in 50 ml of dimethylformamide and mixed with 1.41 g of sodium hydride at 0° C., within 20 minutes, in 3 portions, with vigorous stirring and under argon. After 90 minutes of reaction time at 0° C., it was neutralized with dilute hydrochloric acid, and the solvent was evaporated off in a vacuum. The residue was taken up in 50 ml of ice water and twice extracted with 50 ml each of methylene chloride. The organic phase was dried over $Na_2SO_4$, and evaporated on the rotary evaporator under vacuum. The residue slowly thoroughly recrystallized at room temperature. 8.0 g of product having a melting point of 54° to 56° C. and a content according to GC of 90.8 percent was obtained.

This corresponded to 7.26 g of 100 percent product, which equalled 97.4 percent yield.

EXAMPLE 3

Production of 4-methoxy-3-pyrrolin-2-on-1-yl acetic acid methyl ester

Analogously, there was obtained from 4-methoxy-3-pyrrolin-2-one and bromoacetic acid methyl ester, in dimethylformamide with sodium hydride at 0° C., 4-methoxy-3-pyrrolin-2-on-1-yl acetic methyl ester in 92 percent yield having a melting point of 104° to 106° C.

EXAMPLE 4

Production of 4-methoxy-3-pyrrolin-2-on-1-yl acetic acid benzyl ester

Analogously, there was obtained from bromoacetic acid benzyl ester in acetonitrile with sodium hydride at 0° C., 4-methoxy-3-pyrrolin-2-on-1-yl acetic acid benzyl ester in 95 percent yield having a melting point of 129° to 130° C.

EXAMPLE 5

4-methoxy-3-pyrrolin-2-on-1-yl acetic methyl ester from 4-chloro-3-methoxy-butenoic-2-E-acid methyl ester A suspension of 6.5 g (0.052 mol) of glycine methyl ester hydrochloride in 30 ml of acetonitrile was mixed with a solution of 5.3 g of triethylamine in 10 ml of acetonitrile. It was heated to reflux, and 2.1 g of water-free sodium acetate was added. Then a solution of 4.4 g (0.025 mol) of 4-chloro-3-methoxy-2-E-butenoic-acid methyl ester (content (GC): 95.2 percent) and 20 ml of acetonitrile was added, drop by drop, within 30 minutes. It was stirred again for 4.5 hours with reflux. Then the reaction solution was cooled to 0° C., filtered from the precipitated solid, and the filtrate was concentrated in a rotary evaporator. The residue was picked up in 100 ml of ice water, acidified with 6.0 g of 32 percent hydrochloric acid, and extracted 5 times, each with 100 ml of methylene chloride. The organic solution was dried over $Na_2SO_4$ and evaporated. The residue was recrystallized in 30 ml of carbon tetrachloride. 4.0 g of white, crystalline product having a melting point of 105° to 107° C. (GC content: 96 percent) was obtained. The yield was 81.5 percent.

What is claimed is:

1. 4-Alkoxy-3-pyrrolin-2-on-1-yl acetic acid-$(C_1-C_4)$-alkyl ester of the formula:

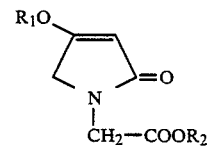

wherein $R_1$ is a $(C_1-C_2)$-alkyl and $R_2$ is a $(C_1-C_4)$-alkyl or benzyl.

2. 4-Methoxy-3-pyrrolin-2-on1-yl acetic acid ethyl ester of the formula:

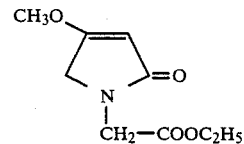

3. The composition comprising 4-methoxy-3pyrrolin-2-on-1-yl acetic acid methyl ester in carbon tetrachloride.

* * * * *

UNITED STATES PATENT AND TRADEMARK OFFICE
CERTIFICATE OF CORRECTION

PATENT NO. : 4,880,940

DATED : November 14, 1989

INVENTOR(S) : Thomas MEUL et al.

It is certified that error appears in the above-identified patent and that said Letters Patent is hereby corrected as shown below:

On the title page, Item [19] should be --Meul,et al--.

The last name of the first inventor, should be changed from "Muel" to --Meul--.

Signed and Sealed this

Thirtieth Day of July, 1991

Attest:

HARRY F. MANBECK, JR.

Attesting Officer

Commissioner of Patents and Trademarks